US007711581B2

(12) United States Patent
Hood et al.

(10) Patent No.: US 7,711,581 B2
(45) Date of Patent: May 4, 2010

(54) CUSTOMIZABLE HANDHELD COMPUTER DATA COLLECTION AND REPORT GENERATION SOFTWARE

(76) Inventors: Andrew David Hood, 14500 Surrey Pl., Pine Grove, CA (US) 95665; Jeffrey Scott Sliwa, 7177 Catalina Isle Dr., Lake Worth, FL (US) 33467

( * ) Notice: Subject to any disclaimer, the term of this patent is extended or adjusted under 35 U.S.C. 154(b) by 1281 days.

(21) Appl. No.: 09/930,788

(22) Filed: Aug. 15, 2001

(65) Prior Publication Data
US 2003/0036684 A1 Feb. 20, 2003

(51) Int. Cl.
*A61B 5/00* (2006.01)
(52) U.S. Cl. .............................. 705/3; 600/300; 704/9; 707/104
(58) Field of Classification Search ................ 705/2–3; 600/300
See application file for complete search history.

(56) References Cited

U.S. PATENT DOCUMENTS

| 5,222,211 | A | | 6/1993 | Mueller et al. | |
|---|---|---|---|---|---|
| 5,640,953 | A | * | 6/1997 | Bishop et al. | ................ 600/300 |
| 5,659,741 | A | | 8/1997 | Eberhardt | |
| 5,682,526 | A | | 10/1997 | Smokoff et al. | |
| 5,772,585 | A | * | 6/1998 | Lavin et al. | .................. 600/300 |
| 5,867,821 | A | * | 2/1999 | Ballantyne et al. | .............. 705/2 |
| 5,924,074 | A | | 7/1999 | Evans | |
| 5,950,168 | A | | 9/1999 | Simborg et al. | |
| 5,953,523 | A | | 9/1999 | Martinez et al. | |
| 6,047,259 | A | * | 4/2000 | Campbell et al. | ............... 705/3 |
| 6,055,494 | A | * | 4/2000 | Friedman | ........................ 704/9 |
| 6,168,563 | B1 | * | 1/2001 | Brown | ......................... 600/301 |
| 6,321,113 | B1 | * | 11/2001 | Parker et al. | .................... 607/5 |
| 6,564,104 | B2 | * | 5/2003 | Nelson et al. | ................. 607/60 |
| 2001/0023316 | A1 | * | 9/2001 | Albert et al. | ................ 600/301 |
| 2002/0118112 | A1 | * | 8/2002 | Lang | ....................... 340/573.1 |
| 2003/0013959 | A1 | * | 1/2003 | Grunwald et al. | ............ 600/437 |
| 2003/0036683 | A1 | * | 2/2003 | Kehr et al. | .................... 600/300 |
| 2004/0220830 | A1 | * | 11/2004 | Moreton et al. | ................ 705/2 |
| 2005/0144182 | A1 | * | 6/2005 | Boris et al. | ................. 707/100 |
| 2005/0197864 | A1 | * | 9/2005 | Koritzinsky et al. | ............ 705/2 |

* cited by examiner

*Primary Examiner*—Vanel Frenel
(74) *Attorney, Agent, or Firm*—Mathew J. Temmerman; Daniel Maguire; Temmerman Law Office

(57) ABSTRACT

A software system for gathering and managing medical patient information is disclosed. The system has two components: a first computer module for gathering medical information using medical data entry screens, and a second computer module for creating customized medical data entry screens. The second module can create and customize virtually all aspect of the medical data entry screens. The present invention also allows users to create natural language reports from the medical data that has been gathered, and these reports can reviewed on the screen or through a print-out. Additionally, the data is stored is stored in database, with unique identifiers assigned to each data point, thereby facilitating data mining. The system also includes a matrix, a unique data entry tool that allows users to easily correlate body parts and modifiers. The system is designed to be used with handheld computing devices, and is especially suitable for use with emergency medical services, although it can be used in a variety of contexts.

17 Claims, 11 Drawing Sheets

Fig. 2

```
SSTART_MDT
Medic 3      1.Donnelly         >
Vehicle 9604  2. Friss-Hertzog

200106230238  Round Trip Transfer  >
   Scene      Agency_bold_12
  Complaints
  Dispatch Enroute   >  List1
   10:26    A
  102,237   V Start  Main  End  Utility
```

Fig. 3

```
Run                Pt. 01 ▼ of ?? ▼
Last                            unk.
First male  >  Date of Birth    1  2  3
female   Demographics     4  5  6
Age 128  Yr. mo. day est. 7  8  9
Wt. 288  lb    kg    est.    0  <-

ADULT    PEDS    Transfer

Start  Main  End  Utility
```

Fig. 4

```
FieldSaver:History Screens  11:04
CC med  traum   chest pain
    chest     bradycardia
  abdomen/uro  tachycardia
  neurological cardiac pmhx/proced
   extremity  - - - Pulmonary - -
   psych/skin SOB
   head/back  CHF exacerbation
    ob/gyn    COPD exacerbation
   symptoms   asthma exacerbation
   diseases   airway obstruction
  tox./habits nicotine addiction
    other     home O2

Main  history  PE  TX  End
```

Fig. 5

```
FieldSaver:Physical Exam  11:07
nl abn.              nl abn.
 □ □ Head            □ □ Neuro
 □ □ Neck            □ □ Skin
 □ □ Chest           □ □ Pelvis/hip
 □ □ Abdomen         □ □ Upper ext
 □ □ Back            □ □ Lower ext
 □ □ Spine
Skin signs           Vascular Signs
   warm        ^      < 3 cap. refill ^
   pink        ^      strong pulses   ^
   Dry         ^      poor turgor     ^

Main  MD  PE  TX  End
```

Fig. 6

```
FieldSaver: Review            11:22
Hood, Drew         42Y  m  2001-1010-01
Chief Complaint:
Chief Complaint: chest pain, shortness
of breath, diabetes.
History:
Chest pain described as fullness,
pressure and tightness and rated as
8/10. Pain pattern noted to be
worsening and exertional and lasting
for 30 minutes. Chest pain located at
substernal area and radiates to the
neck and left arm. Symptoms like prior
angina. Chest pain improved by NTG
sl, oxygen and rest and chest pain
worse with exertion. Patient has
shortness of breath with exertion.
  <<       PCR      Billing
```

Fig. 7

```
Chest Pain 1 of 2             11:27
Ch. pain desc.  [!]  ..and rated as  [!]
fullness         ▲  10/10      ▲
pressure            9/10
tightness           8/10
aching              7/10
stabbing            6/10
severe          ▼   5/10       ▼
Pain      [!]    worsening     ▲
  Pattern        crescendo
  ..lasting for  exertional
  Located at     positional
  ..radiates to  ascending
  Like prior     resolved
                 associated w/ food ▼
  MD    Hx    ch.pain1  ch.pain2
```

Fig. 8

```
Chest Pain 2 of 2             11:28
CP improved by  [!]  ..and worse with [!]
NTG sl          ▲  exertion        ▲
oxygen             eating
rest               positions
burping            lying down
antacids           deep breaths
nothing         ▼  leaning forward ▼
Pt. has SOB with [!]  Noted        [!]
exertion            diaphoresis    ▲
chest pain episodes weakness
with lying flat     nausea
both rest and activity vomiting
                    epigastric pain
                    anxiety        ▼
  MD    ch.pain1  ch.pain2   SOB
```

Fig. 9

```
Syncope                       11:29
History of      [!]  ..preceeded by [!]
witnessed           no symptoms    ▲
unwitnessed         dizziness
syncopal event      palpitations
near syncope        light-headedness
                    diaphoresis
                    SOB            ▼
Noted    [!]    unconscious
  Pt. desc. as  confused
  ..lasting     unresponsive
  Associated    obtunded
  Cardiac sx.   staring spell
  History of
  MD    Hx    syncope    Hx
```

Fig. 10
Fig. 11
Fig. 12
Fig. 13

Fig. 14.

CUSTOMIZABLE HANDHELD COMPUTER DATA COLLECTION AND REPORT GENERATION SOFTWARE

BACKGROUND OF THE INVENTION

1.) Field of the Invention

The present invention relates to customizable computer software for use in collecting, managing, and analyzing patient medical data.

2.) Background of the Invention

Traditionally, patient medical data has been gathered and stored using paper-based systems. With the advancement of computer technology, many hospitals and other collectors of patient medical data have sought to automate their processes for gathering and managing such data. Thus, handheld computing devices have recently been used to gather and manage patient medical data. For instance, software has been developed to enable handheld computing devices to be used by paramedics and other providers of emergency medical services ("EMS"). This software is typically pre-programmed so that the EMS provider is prompted to gather pertinent information, such as the patient's name, chief complaint, etc.

Existing patient medical record software is only customizable to a limited extent. Such software typically only allows the EMS provider or administrator to change or edit features in a pre-existing data-entry screen. For instance, existing medical record software may allow EMS providers to edit the adjectives for severity of pain, or edit a list of conditions.

However, there is a strong need for greater customization. For instance, EMS providers may need to create or customize data collection screens on the data-gathering software for a future or ongoing study, or for use by a regulatory agency. The data-gathering software might also need extensive changes because of a regional health situation (such as an outbreak of a particular disease), or because of changes in medical knowledge. For, example, the software might be customized to gather information about Viagra use in patients with chest pain, since that drug may have adverse reactions with nitroglycerin, which is the standard therapy for chest pain. As explained below, the present invention provides a software tool (not just a database) that enables administrators to completely customize their data-gathering software.

The present medical data software also lacks a straightforward way to handle multiple modifiers pertaining to a particular body part, such as an ankle that is "strained," "swollen," and "lacerated." The present invention provides a unique "matrix," which allows EMS provider to intuitively gather such information.

Finally, the current software is not able to integrate two functions: the generation of natural language reports, and the storage of data in a database, which allows for complicated data queries and data mining. Instead, existing software supports one or the other of these functions, but not both. Thus, there is a need for software that stores the patient medical data in a database, but also generates natural language reports.

BRIEF SUMMARY OF THE INVENTION

The present invention is an integrated medical data software application. The invention consists of two parts, "Field Saver" and "Template Manager." FieldSaver is a data gathering and management program, which is designed to be used by EMS providers in the field on handheld computing devices. It has a number of different data entry screens that prompt the EMS provider to gather specific information.

The EMS provider can navigate backwards and forwards through the screens, and certain screens are activated based upon answers to previous questions. For instance, if the EMS provider indicates that the subject has chest pain, then FieldSaver activates two "chest pain" screens that prompt the EMS provider for more specific information, such as a description of the pain (aching, stabbing, severe, etc.), and the severity of the pain, on a scale of 1-10. FieldSaver also has matrices to gather multiple modifiers related to multiple body parts.

The program is designed to minimize the amount of information that the EMS provider must input by typing. Thus, for almost fields, the EMS provider must simply select the proper data from a list box, button, or matrix. Each data point—such as the subject's weight, or his chief complaint, or the description of a pain felt in his abdomen—will be referred to as an item.

The EMS provider typically selects items by picking from a "list box" containing multiple choices. So, for instance, if the subject reports chest pain, the EMS provider can select from a list box specifying whether the pain is described as "aching" or "squeezing" and so on. The EMS provider can also manually input data by using the character recognizer on the handheld computing device or by typing any item into the list box.

In use, FieldSaver receives information about a particular EMS call through remote transmission, and can starting populating screen items based on information received from the call, such as the patient's name, address, etc.

Upon arriving at the scene, the EMS provider could then use FieldSaver to gather all necessary data from the call. When the call is complete and all data has been gathered, the EMS provider could then generate a natural language report from the data. Using a portable printer, the EMS provider could print out the report from the emergency vehicle, and provide it to the hospital. The information could also be transmitted from the handheld computing device directly to the hospital or other data collection point, using any of the remote transmission conduits described below.

Once the data has been electronically captured in the handheld computing device, it could be used in many different ways. For instance, the data can be used as part of medical study, for billing purposes, or for analysis by regulatory agencies such as the National Highway Safety Transportation Board or local regulatory bodies. Indeed, FieldSaver can be specifically programmed to gather categories of information that may be needed for such particular purposes.

Template Manager is a software tool that creates customized medical data entry screens for the FieldSaver application. The Template Manager can create new FieldSaver screens, and can edit, delete, or duplicate existing screens. In creating new screens or "instances," the EMS provider can choose from a number of "templates," which provide particular arrangements of labels, buttons, list boxes, and matrices.

Using Template Manager, an administrator can create and customize virtually all aspects of FieldSaver, by (i) adding, removing, or re-ordering items in a list, (ii) changing screen titles, labels, and the captions on buttons, (iii) changing the text that is displayed in a report when a particular item is selected, (iv) determining the syntax and structure of particular items in reports, (v) specifying whether a particular list box allows for single select or multiple select, (vi) specifying identifiers for lists and list items, (vii) "flagging" items that will be useful for specific purposes, such as advanced life support indicators, (viii) for some templates, specifying categories for each list item, so that subsets may be displayed, and (ix) for some templates, specifying screens to be displayed when a particular item is selected.

BRIEF DESCRIPTION OF THE DRAWINGS

FIG. 2 is a screen shot showing the start screen for FieldSaver.

FIG. 3 is a screen shot showing the "main" screen for FieldSaver.

FIG. 4 is a screen shot showing the primary history screen for FieldSaver.

FIG. 5 is a screen shot showing the physical examination screen for FieldSaver.

FIG. 6 is a screen shot showing a review screen for FieldSaver.

FIG. 7 is a screen shot showing the first chest pain screen for FieldSaver.

FIG. 8 is a screen shot showing the second chest pain screen for FieldSaver.

FIG. 9 is a screen shot showing a syncope screen for FieldSaver.

FIG. 10 is a screen shot showing a shortness of breath screen for FieldSaver.

FIG. 11 is a screen shot showing a treatment screen for FieldSaver.

FIG. 12 is a screen shot showing the end screen for FieldSaver.

FIG. 13 is a screen shot showing the utility screen for FieldSaver

FIG. 14 is a screen shot showing a matrix in FieldSaver.

DETAILED DESCRIPTION

Figure 1:
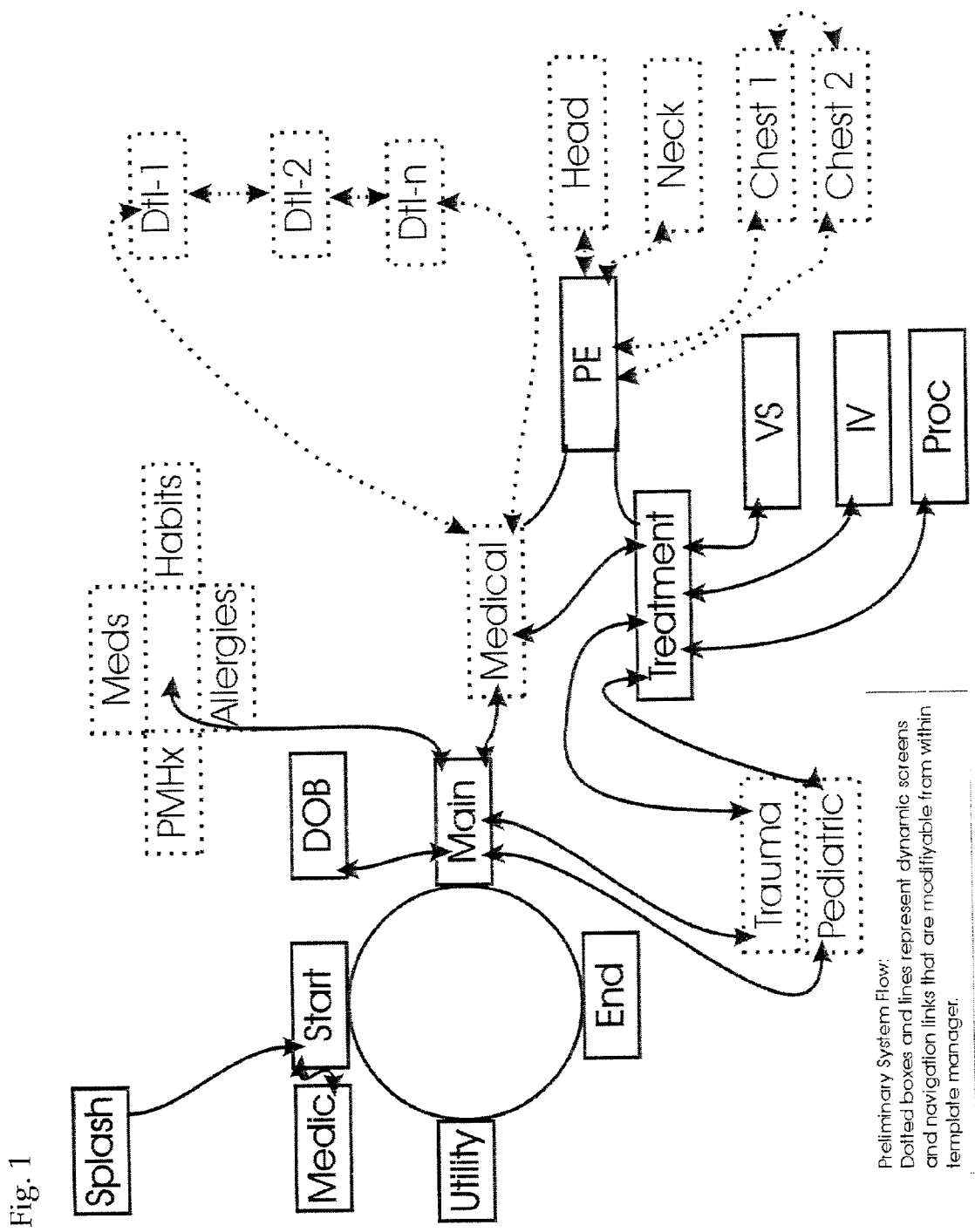
FIG. 1 shows the system flow of screens for FieldSaver.

The present invention has two parts: a data gathering and management program, (FieldSaver), and a tool for customizing the data gathering and management program (Template Manager). Both of these modules are described in detail below.

FieldSaver can be used by paramedics and other EMS providers to gather and manage patient medical information. It displays a series of screens to prompt the EMS provider to enter appropriate patient information. Thus, in addition to its data gathering and management function, the program also can be used for training, since it guides the EMS provider to gather the information that is needed for proper diagnosis and treatment.

As depicted in FIGS. 1-14, FieldSaver presents EMS providers with a series of screens pertaining to particular aspects of the EMS call. The EMS provider can navigate back, forth, and between screens.

The screens have a number of features for data gathering and management. The screens typically have a screen title, such as "Start," "Main," or "Chest Pain 1." The screens may also have screen labels that describe particular subparts of a screen. For instance, the Physical Exam screen, FIG. 5, has a screen label denoting the "Skin signs" portion of that screen.

Patient data can be entered into screens in a number of ways. A few items, such as the patient's name, must be typed in or inputted using a character recognizer, if the information has not already been entered electronically via remote transmission. (See. FIG. 3). But for most all other items, the EMS provider can simply select the appropriate data from a list box or matrix.

For instance, the history screen, FIG. 4, contains a series of buttons on the left side of the screen. The first two buttons denote whether the program is currently collecting medical related history, or trauma-related history. If the EMS provider selects the medical button, then the program displays a series of buttons corresponding to various medical categories, such as chest problems, neurological problems, etc. The EMS provider can then select the appropriate buttons corresponding to the patient's medical history, and the list box to the right will then display a number of possible descriptions of the problems. For instance, if the EMS provider selects the 'chest' category button, then he can choose the particular type of chest problem from the list box, such as bradycardia. After the EMS provider has finished entering the data for a particular category, that category is highlighted to show it has been chosen.

Some of the boxes are "single select," meaning that the EMS provider can only select one item from the list. For instance, in FIG. 7, the chest pain screen, the EMS provider can enter data concerning the severity of the chest pain, ranked on a 1 to 10 scale. This box is single select, since there can only be one level of severity. However, most boxes are multiple select, meaning that the EMS provider can select more than one item from the list box. For instance, in FIG. 7, the EMS provider can enter a number of items to describe the patient's chest pain, such as "fullness," "pressure," etc. Many list boxes can by augmented in FieldSaver by pressing the exclamation mark within the box, as shown in FIGS. 7-10. By pressing this button, the EMS provider can add new choices to the list box.

FieldSaver also includes a novel data entry means called the matrix. This tool, depicted in FIG. 14, allows the EMS provider to quickly select multiple modifiers pertaining to a particular body part. For instance, using the matrix, the user can designate "bruising," "abrasion," and "tenderness" in the left flank of the abdomen simply by pressing buttons corresponding to that body part and those modifiers.

Many of the screens are linked, so that whenever a EMS provider indicates a particular medical condition, another screen is automatically displayed. For instance, if the EMS provider indicates that the patient has chest pain, then the EMS provider will be prompted to fill out two additional chest pain screens, seeking more particularized information. (FIGS. 7 & 8).

The system flow for FieldSaver is depicted on FIG. 11n this flowsheet, "PE" stands for physic exam, "VS" stands for vital signs, "PMHx" stands for patient's medical history, "Dtl" represents detail screens addressing specific medical data, and "IV" stands for intravenous. As described below, the links between screens can be modified using Template Manager.

The first substantive screen in FieldSaver is the start screen, depicted on FIG. 2. This screen gathers certain basic data, such as the name of the EMS provider, the run number, directions to the call location, and the patient's complaint. Much of this information could be populated on the screen when the call is received, by wireless transmission from the call center. To accomplish this remote transmission, a number of conduits could be used, such as infrared, wireless LAN, or cellular modem IP over cellular. At the current time, the preferred method of remote transmission from ambulances is a CDPD (cellular digital packet data) modem to third party CAD (Computer Assisted Dispatch) 911 system.

Using the start screen, the EMS provider can indicate the type of call (Code 2, Code 3, ALS transport, Round trip transfer etc.) by clicking on the corresponding button, thereby activating a pop-up screen listing the various call types.

The next screen, depicted on FIG. 3, is the main screen. The EMS provider can navigate to this screen by pressing the "main" button on the navigation bar at the bottom of the start screen. The main screen acts like the center of a spoke, by linking to a number of other screens. This screen gathers basic biographical patient data, such as name, date of birth, age, height, weight, etc. It also allows the EMS provider to select the type of problem that prompted the call, divided into three categories: pediatric, adult, transfer. The main screen also links to a date selector screen, which allows the EMS provider to select the patient's date of birth by pressing buttons corresponding to the day, month, and year of the patient's birth.

Once the EMS provider has selected the category of the call (i.e. adult, transfer or pediatric), the program then displays the history screen, as depicted in FIG. 4. This screen gathers information about the patient's medical history, divided into two categories: history of medical problems, and history of traumas. When the "med" button is pushed, the program lists a series of sub-categories of potential medical problems, such as "chest," "abdomen/uro," etc. When the EMS provider presses the button related to the particular sub-category, the list box to the right displays a list of potential problems. So, for instance, if the patient has a history of bradycardia, the EMS provider would select "med," then "chest" then "bradycardia."

After the EMS provider has entered patient medical information, a review screen can be displayed, reflecting the information gathered thus far in a natural language sentence, such as "Chest pain described as fullness, pressure, and tightness and rated as 8/10." FIG. 6.

Next, the EMS provider can navigate to a physical examination screen, as depicted in FIG. 5. This screen allows the EMS provider to store data gathered during physical examination of the patient. As depicted in FIG. 5, the program allows the EMS provider to check whether various parts (head, neck, and chest, etc.) are normal or abnormal. The screen also allows the EMS provider to note the patient's skin and vascular signs.

If the EMS provider has indicated abnormality in a certain body region, a separate screen for that body part may be displayed. For instance, if the EMS provider indicates problems with the abdomen, a screen specific to that region will be displayed. The screen may use a matrix to correspond body parts to modifiers, such as is displayed in FIG. 14. As shown in that screen shot, the matrix will allow the EMS provider to indicate multiple conditions of specific body parts by pressing a few buttons. So, to indicate bruising and abrasions in the right lower quadrant of the abdomen, the EMS provider would simply click the "RLQ," "bruising," and "abrasion" buttons. After finishing the screen, the EMS provider can navigate back to the physical examination screen.

After the physical examination screen, the treatment screen can be displayed. (FIG. 11). This screen allows the EMS provider to record the time of treatment, and who provided it. This screen also links to other screens that capture the patient's vital signs, any procedures performed (airway clearing, splinting, spine care, etc.), any intravenous fluids provided, and any drugs provided. It also links to a screen that allows the EMS provider to provide a narrative of the care provided and related details.

The program also provides an end screen, FIG. 12, that is used to record data pertinent to the conclusion of that call, addresses, data concerning billing information, and an indication whether other forms should be completed. For instance, if the call involved hazardous materials, the EMS providers could indicate that a "Haz. Mat." form must be filled out.

From the end screen, the EMS provider can review all the information entered, by pressing the review button. This review, which is depicted in FIG. 5, is a natural language collection of all the information collected, organized into sentences. The review can also be printed out in a fuller format. When viewed on the screen, many terms are abbreviated, but the hard copy version will typically be displayed without abbreviations. The report can also be beamed to the hospital or data center, using a remote transmission conduit as described above.

In addition to supporting natural language reports, Field-Saver also stores the patient information in a database, so that administrators and researchers can perform complicated data queries, and can use the information for data mining.

There is also a utility screen, FIG. 13, which allows the EMS provider to perform various utility functions. This screen allows the EMS provider to review all calls for that day, to delete all data for a particular call, and to add a new call. This screen displays each call stored on the handheld computing device by call number (entered in the start screen) and date. It also indicates which EMS provider was responsible for which call.

FieldSaver was coded with Embedded Visual Basic and Visual Basic. In its preferred embodiment, it runs in the Windows CE operating system, on any handheld computing device classified as a "Pocket PC," with a screen of 320×240 pixels.

The second part of the present invention is a software tool, called Template Manager, that can create fully customized versions of FieldSaver. While FieldSaver is designed for use on a handheld computing device by paramedics and other EMS personnel, Template Manager will typically be used on a personal computer by an end user content expert, who will customize FieldSaver for a particular group of users. Like FieldSaver, Template Manager is coded using Visual Basic, and is compatible with the Windows operating system.

Figure 15:
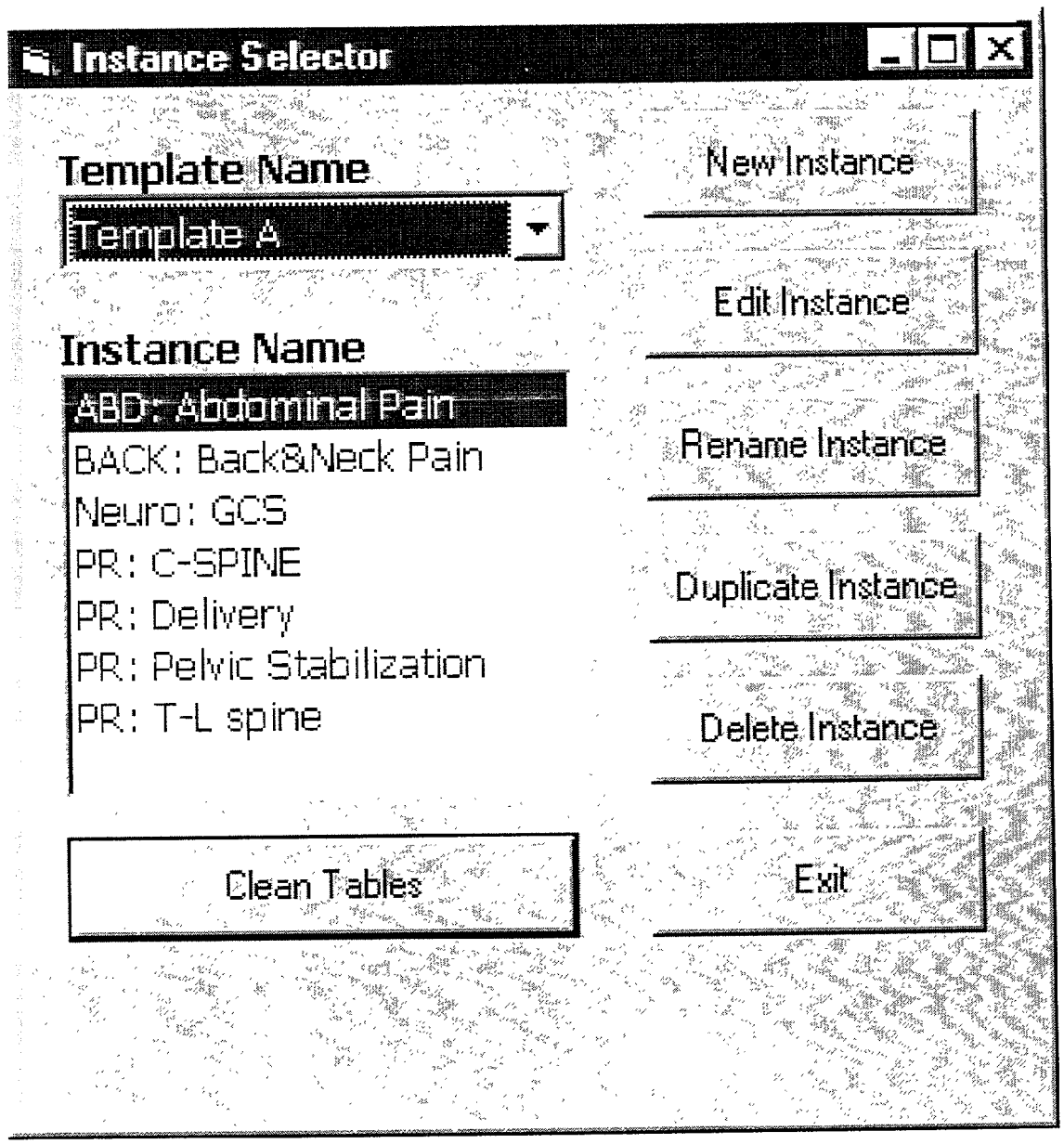
FIG. 15 is a screen shot showing the instance selector in Template Manager.
Figure 16:
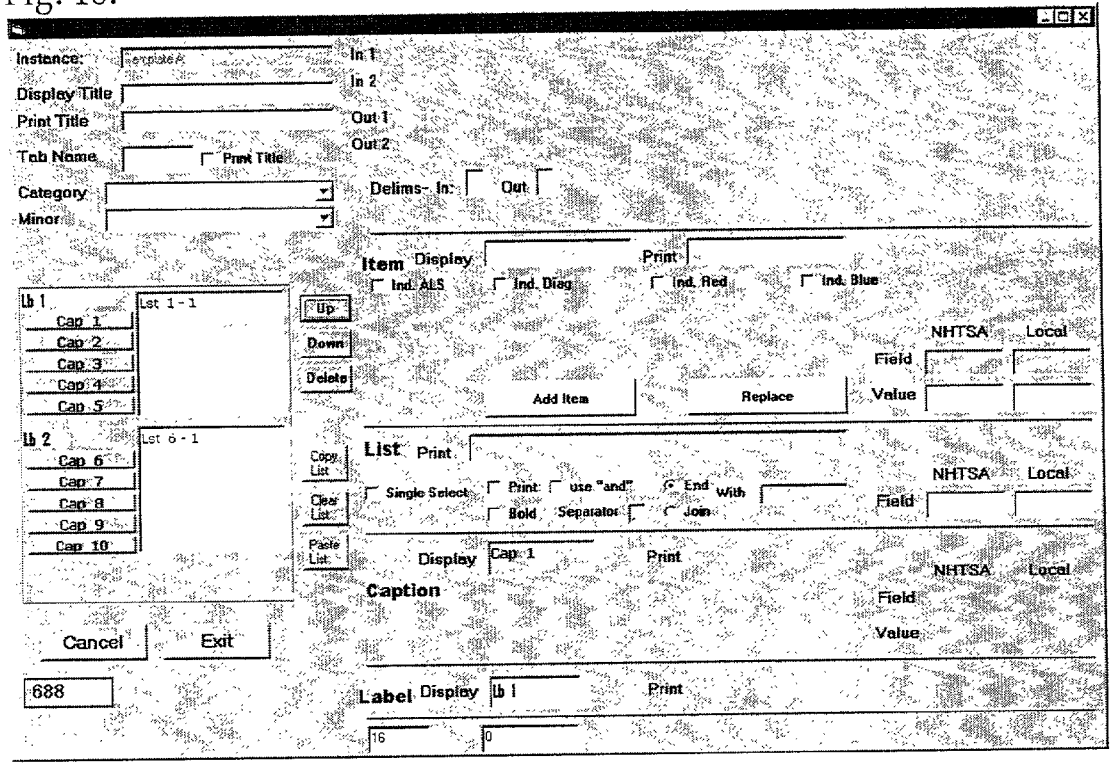
FIGS. 16-25 show various template screens that are available to create instances in Template Manager.
Figure 17:
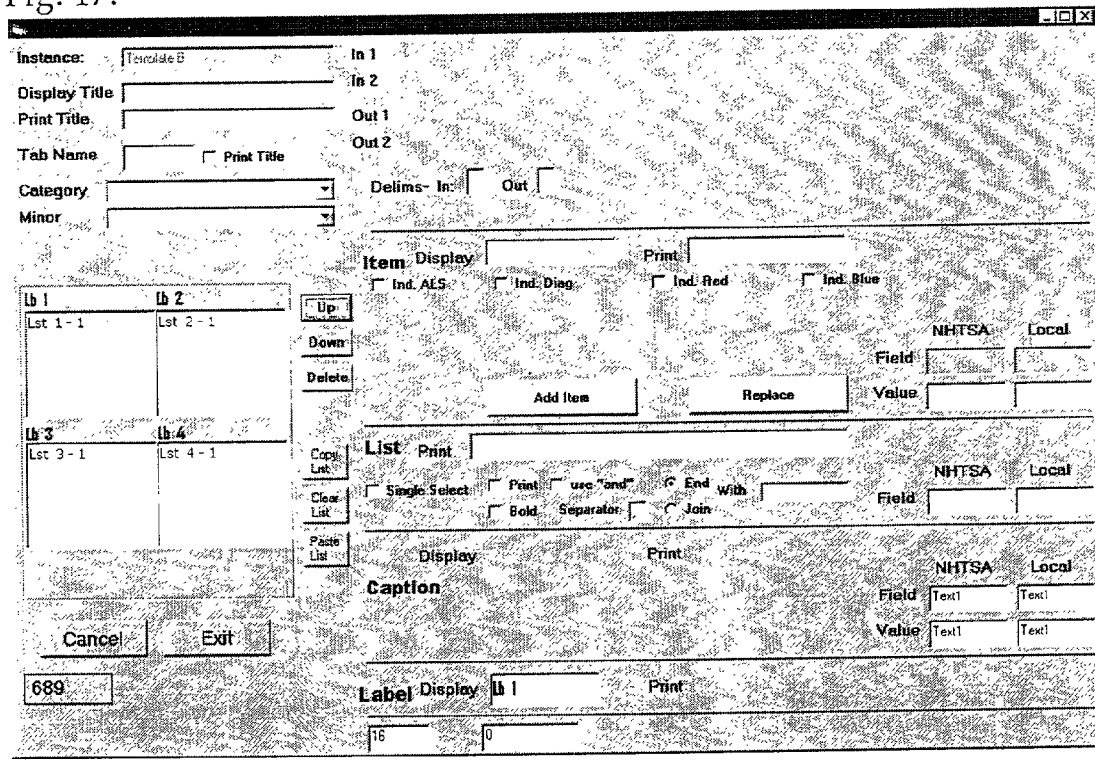
Figure 18:
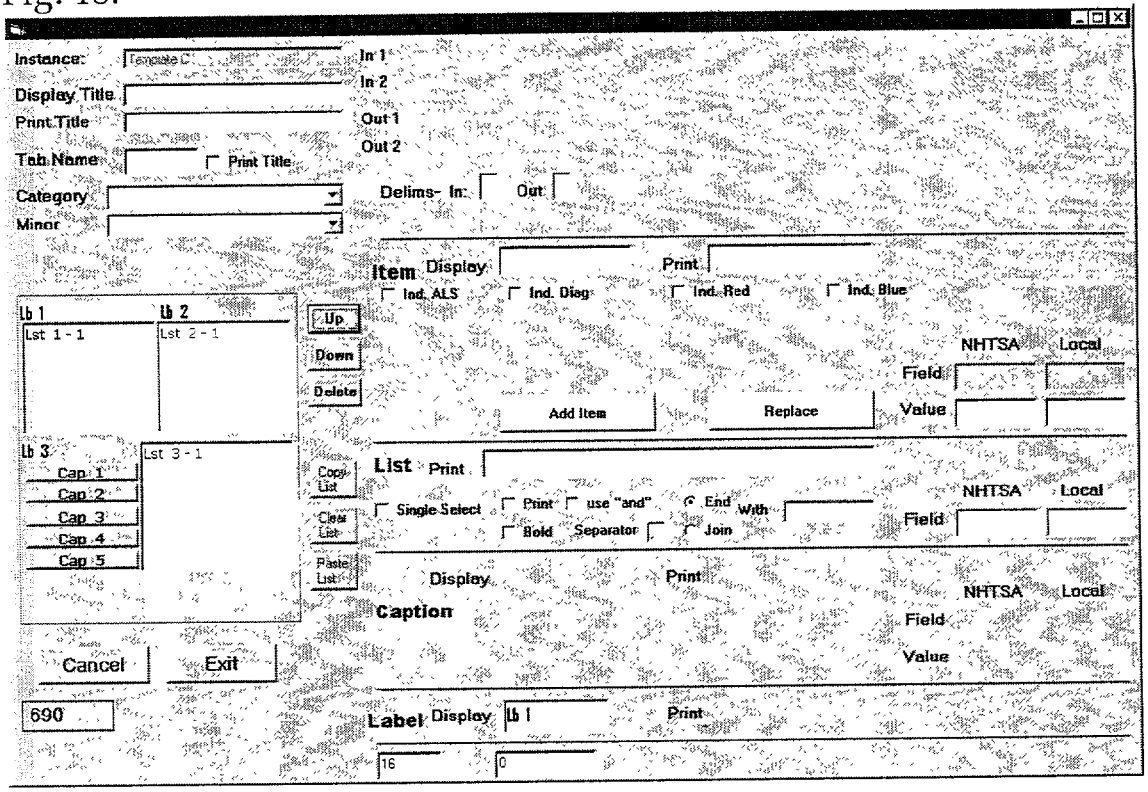
Figure 19:
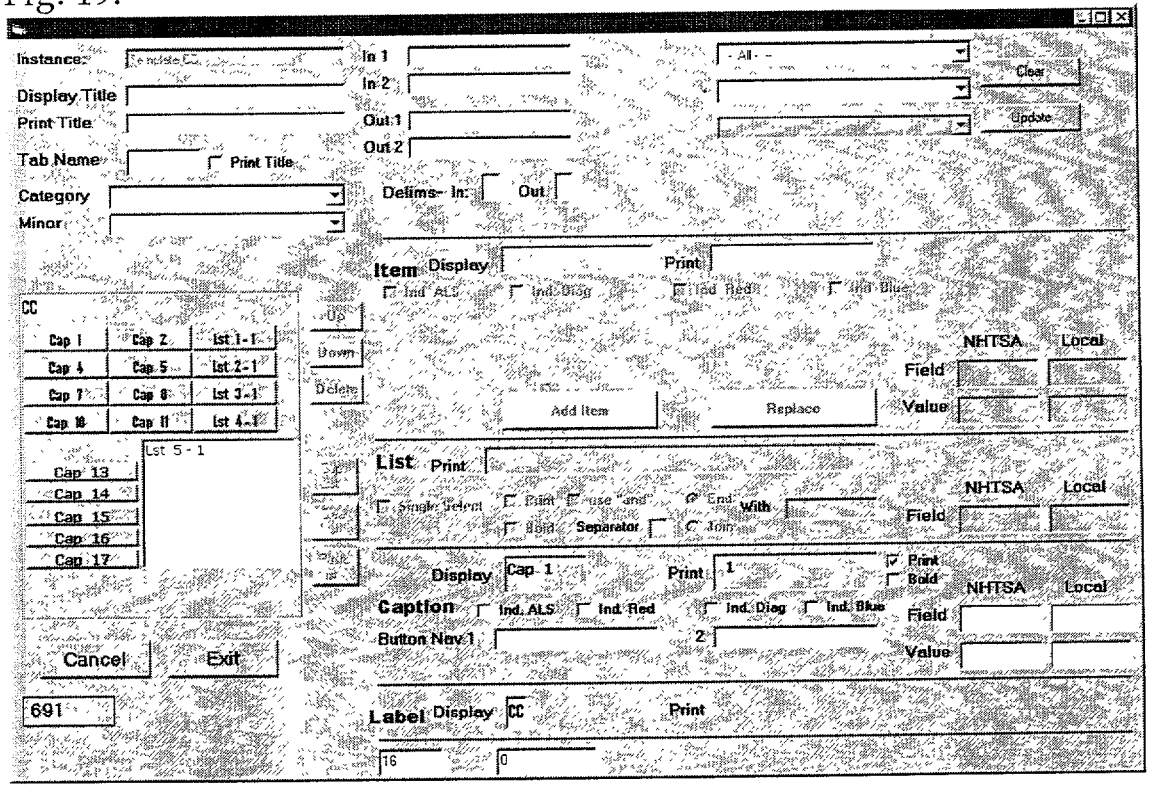
Figure 20:
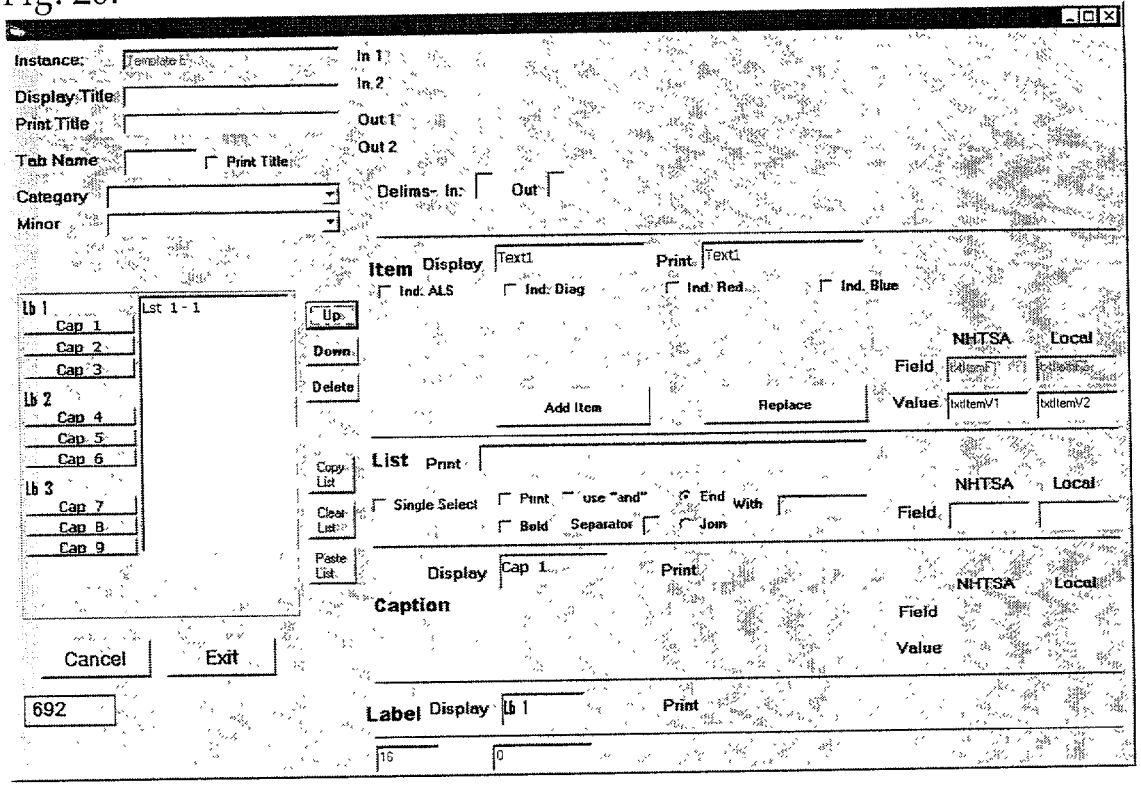
Figure 21:
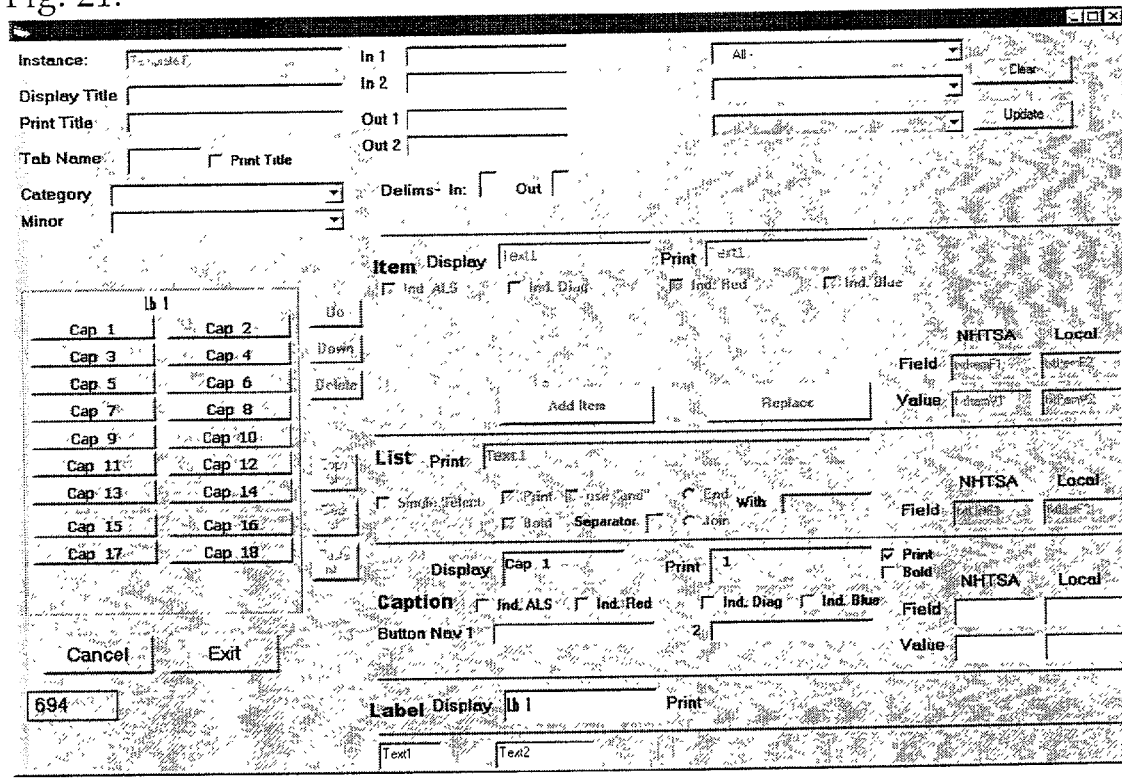
Figure 22:
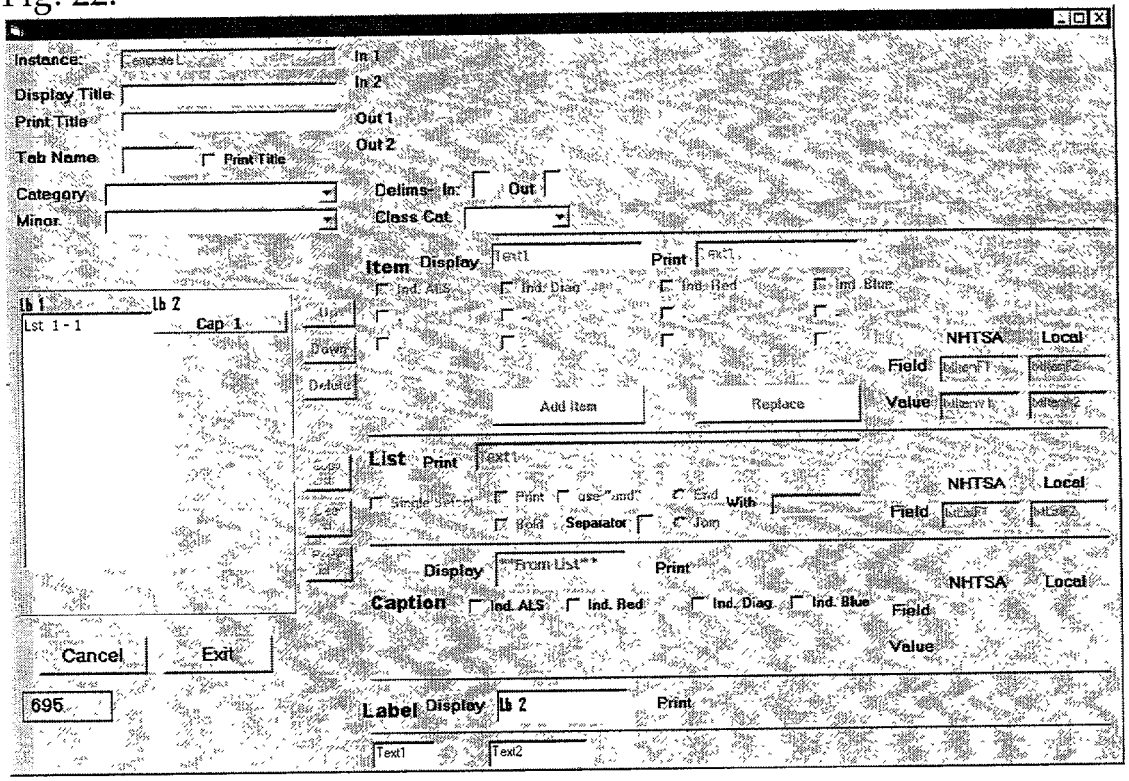
Figure 23:
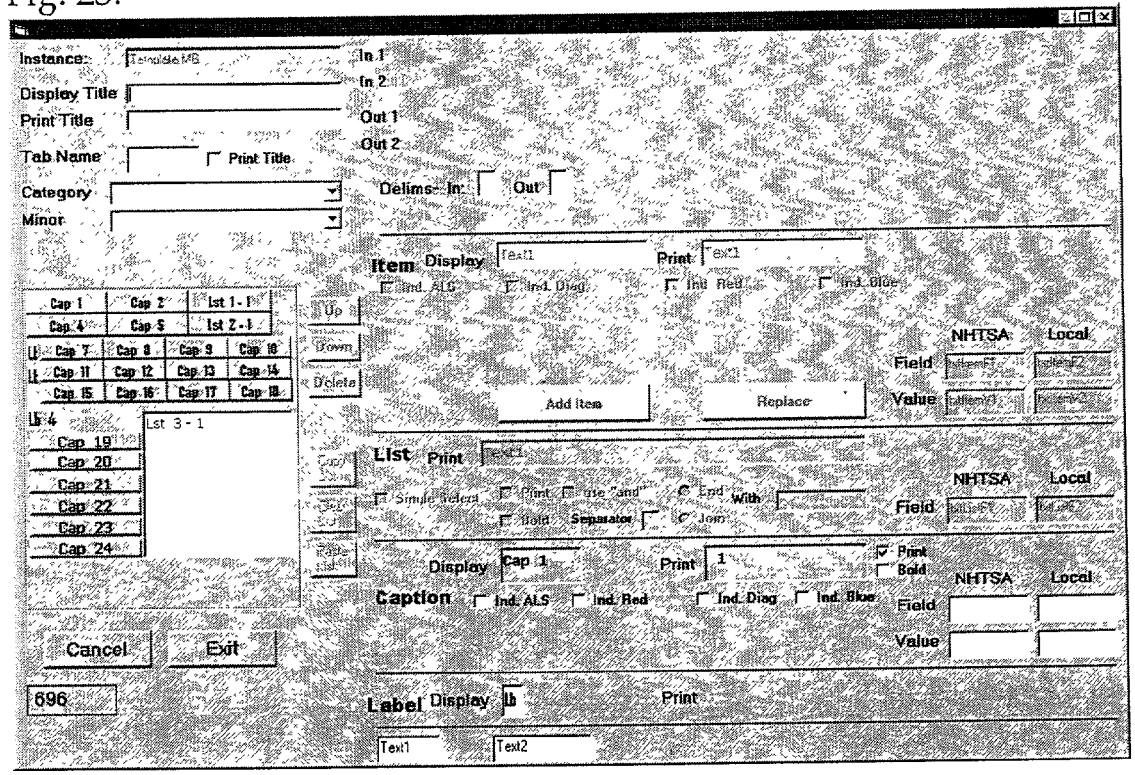
Figure 24:
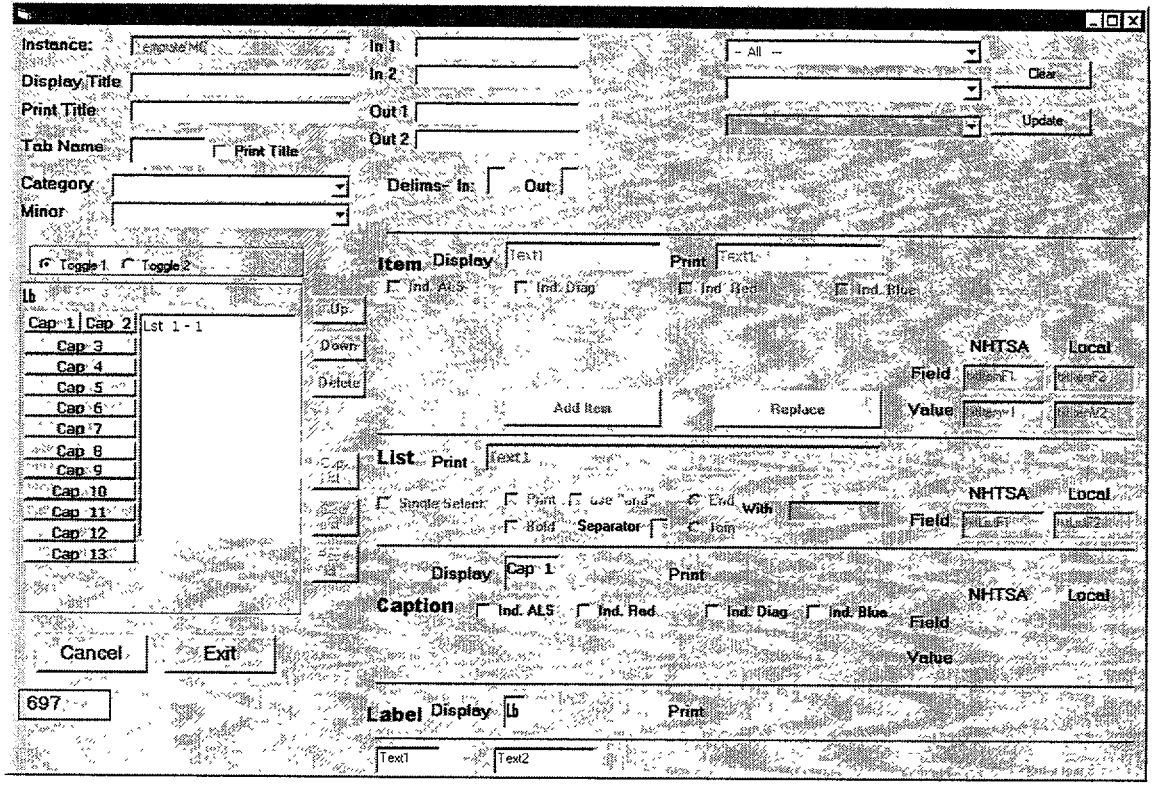
Figure 25:
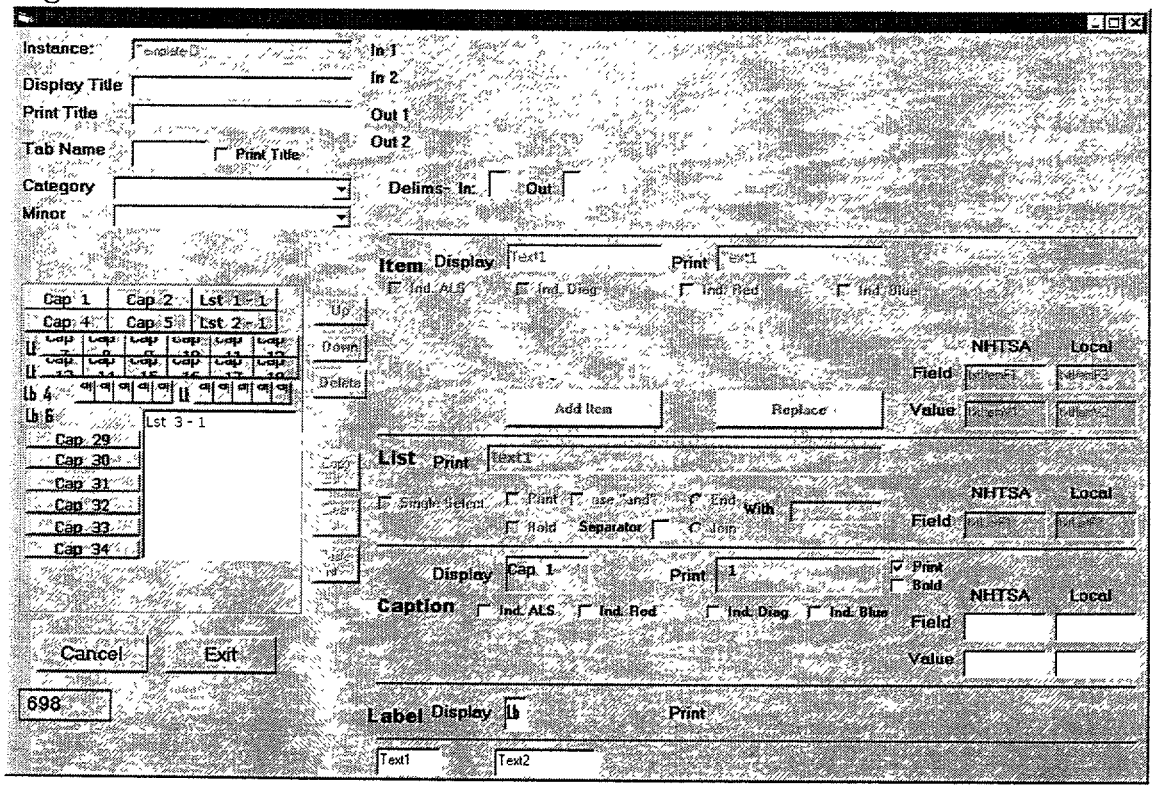

Template Manager presents the user with two different types of screens. The first, labeled instance selector, allows the user to select whether to create a new screen or "instance," or to edit, rename, duplicate, or delete an existing instance. See FIG. 15. The term 'instance' is used to denote the fact that each such screen is derived from one of the templates provided by template manager. Using the instance selector, the user can also provide a name for a new instance, and can choose which one of the various templates should be used to create the new instance. There are currently ten such templates, each of which contains a different layout of buttons, list boxes, labels, and in some cases, matrices. See FIGS. 16-25. The user can select whichever template seems most appropriate given the nature of the new instance.

The next screen allows the user to customize all aspects of the instance. The user can specify the title of the instance, and can decide how the screen should be designated on the tab button on the bottom of FieldSaver, using the "tab name" button. See e.g. FIG. 17. The user can specify where the screen fits within the overall scheme of FieldSaver, by using the "category" button to specify the general category (such as adult, pediatric, or transfer), and can use the "minor" button to identify the sub-category.

The user can also completely customize the list boxes. By pressing the "label" button, the user can specify the desired name for the label. See e.g. FIG. 17. The user can also customize the captions (labeled with placeholders such as cap 1, cap 2, etc.), by highlighting the caption to customized, then typing in the desired text in the provided input box. See e.g. FIG. 16. The user can decide whether the text on a caption should look the same on the screen and on a print out. (Users may use decide to use abbreviations on the screen, but not in the print out).

The items in the list box can also be customized by pressing on the appropriate caption button, then pressing the button for "add item," and then typing in the description of the desired item in the input box. As can be seen on FIG. 16, two input boxes can be provided for describing list items, one controlling how the item will appear when displayed on the handheld computing device (often abbreviated), the other controlling how the item will appear when printed out. Users can also flag particular items as relevant for particular purposes, such as "ALS" (advanced life support), or code red. By flagging these items, the report can display the significance of particular items and flag them for easy data mining later, or add them to a specific list. For example, if an item is flagged diagnosis 'DX' then it can be listed in the diagnosis list for the end user to pick as a final diagnosis instead of having to go and search for it from a list. Particular items can also be designated as relevant to data that must be gathered for the National Highway Transportation Safety Board (NHTSA), or for any local regulatory body. For instance, the NHTSA keeps track of how many traffic accidents victims are wearing seat belts (restraints). This data is collected in FieldSaver when it is chosen from a list on the MVC (motor vehicle collision) screen. The data will print with the report, and then Template Manager will be able to directly field map this information into the appropriate field with the appropriate value in a NHTSA report.

Using Template Manager, a content expert can add new data points or items. Each such item, whether new or preexisting, is automatically given a unique numerical identifier by Template Manager. This unique identifier is very helpful for data mining purposes, since it allows for complicated data queries.

Template Manager also allows the content expert to control the navigation between and among screens. So, for instance, after adding a new item relating to snake bites by a particular species, the content expert can designate that anytime the user selects that item, a new screen will be displayed, seeking more particularized information.

The program also allows the user to designate that a listing is "single select," meaning that the FieldSaver user can only select one item from the list, or "multiple select," meaning that the user can select more than one item from the list. For instance, in describing the severity of chest pain on a scale of one to ten, only one numerical value can be chosen. See FIG. 7.

Additionally, Template Manager allows the content expert to control the syntax and structure of reports, using the "List" portion of the Template Manager screen. See e.g. FIG. 17. This feature allows the content expert to decide whether to use "and" or another separator between items, and whether to end with a period after the last item, or to join the selected list with other data using a specific conjunction.

Figure 14:
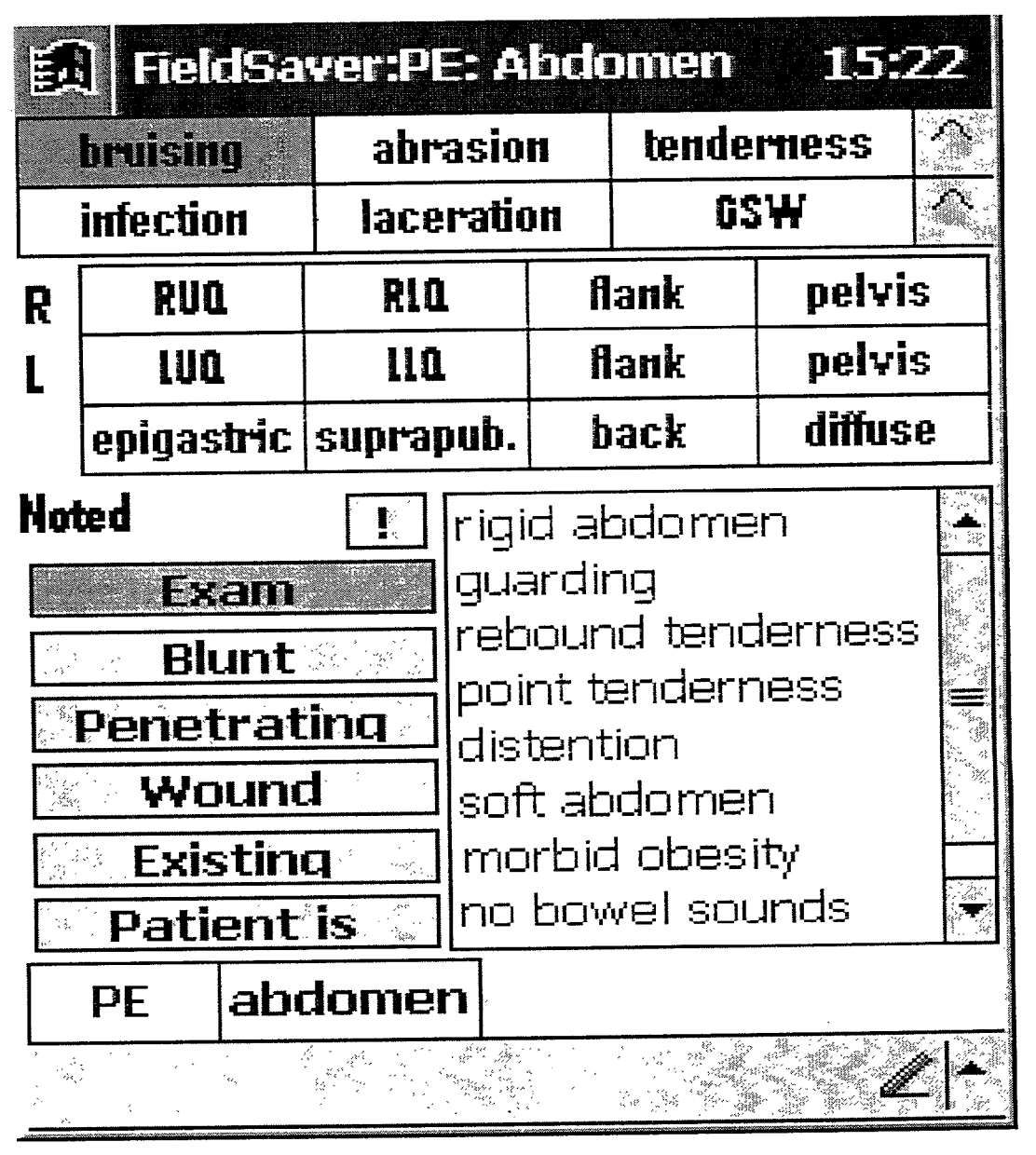

Template Manager also allows users to set up matrices, as shown in FIG. 14. By creating a new matrix, the content expert can correlate any body part with any set of modifiers.

For some templates, Template Manager allows the user to specify sub-lists under particular list items, so that after choosing a list item, a FieldSaver user can input more specific information. See FIG. 22.

The output of Template Manager is a file, sys.data, that is loaded onto each handheld computing device that is running FieldSaver, to create customized versions of FieldSaver.

The present invention can be written as two separate computer programs, or as two modules within a single system. For purposes of this patent, the term "computer module" will include both a stand-alone program, and a discrete module within a system. In its preferred embodiment, the present invention is considered an integrated system with two modules.

One skilled in the art will appreciate that the present invention can be practiced by other than the described embodiments, which are presented for purposes of illustration and not limitation.

We claim:

1. A system for gathering and managing patient medical data in which a handheld computing device has a computer-readable medium having stored thereon a plurality of instruction sequences, which, when executed by a processor, cause the process to perform the steps of:

executing a first module for gathering patient medical information, wherein said first module displays a plurality of customized template based data entry screens, a means for receiving medical data through remote transmission, and a means for creating a natural language report and a data point-based searchable database from said medical information, said natural language report having syntax and structure;

creating said customized template based data entry screens from customized template based data entry screen data received from a template manager having a means for substantially customizing said customized template based data entry screen data for use by said first module;

wherein at least one of said customized template based data entry screens correlates a set of modifiers to a body part; and wherein said customized template based data entry screen data directs the function of said first module.

2. The system according to claim 1, wherein said template manager additionally comprises a plurality of templates for creating said customized template based data entry screens.

3. The system according to claim 2, wherein said template manager additionally comprises means for editing all aspects of said customized template based data entry screens, said syntax and structure of said natural language report, and said data-points.

4. The system according to claim 3, wherein said first module additionally comprises means to delete at least one of said customized template based data entry screens.

5. The system according to claim 3, wherein said template manager has means for customizing navigation between said plurality of customized template based data entry screens.

6. The system according to claim 5, additionally comprising a portable printer for printing out said natural language report.

7. The system according to claim 6, wherein said template manager has a means for flagging certain data items as relevant for specific purposes.

8. The system according to claim 7, wherein said searchable database has a plurality of items, and wherein each such item has a unique identifier, and wherein said customized information further comprises said unique identifier.

9. A software application for gathering and managing patient medical data, comprising:

a first module for gathering patient medical information on a handheld computing device, said first module having a plurality of customized template based data entry screens, a means for receiving medical data through remote transmission, a means for receiving customized information, and a means for creating a natural language report and a data point-based searchable database from said medical information, wherein said natural language report has a syntax and a structure;

a template manager for creating customized template based data entry screens for use by said first module;

wherein the function of said first module is directed by said customized template based data entry screens; and wherein at least one of said customized template based data entry screens allows a user to correlate a set of modifiers with a body part.

10. The software application according to claim 9, wherein said template manager additionally comprises a plurality of templates for creating said customized template based data entry screens.

11. The software application according to claim 10, wherein said template manager additionally comprises means for editing all aspects of said customized template based data entry screens, said natural language report, and said data points in said data point-based searchable database.

12. The software application according to claim 11, wherein said first module additionally comprises means to delete at least one of said customized template based data entry screens.

13. The system according to claim 12, wherein said template manager has a means for customizing navigation between said customized template based data entry screens.

14. The software application according to claim 13, wherein said template manager has a means for controlling the syntax and structure of said natural language report.

15. The software application according to claim 14, wherein said searchable database has a plurality of items, and wherein each such item has a unique identifier, and wherein said customized information further comprises said unique identifier.

16. A system for creating customized medical data input screens, comprising:

a handheld computing device, said handheld computing device having loaded in memory a first module for gathering patient medical information, said first module having a customized medical data entry screen, said screen allowing a user to input patient medical information;

a means for creating a natural language report and a searchable database from said medical information;

a second module having a means for customizing said screen, said natural language report, and said searchable database; and wherein said customization means is template based.

17. A system for gathering and managing patient medical data, comprising:

a handheld computing device, said handheld computing device having a means of gathering specified regulatory data and having loaded in memory a computer module for gathering patient medical information, said module having a customized medical data entry screen, said screen allowing a user to input patient medical information;

a matrix within said data entry screen, said matrix allowing a user to correlate a body part with a set of modifiers;

a second module having a means for customizing said customized medical data entry screen and said matrix; and wherein said customization means is template based.

* * * * *